(12) United States Patent
Schmidt et al.

(10) Patent No.: US 7,888,537 B2
(45) Date of Patent: Feb. 15, 2011

(54) SOLID ACID CATALYST AND PROCESS FOR DECOMPOSITION OF CUMENE HYDROPEROXIDE

(75) Inventors: Robert J. Schmidt, Barrington, IL (US); Deng-Yang Jan, Elk Grove Village, IL (US); Raelynn M. Miller, LaGrange, IL (US); James A. Johnson, Clarendon Hills, IL (US)

(73) Assignee: UOP LLC, Des Plaines, IL (US)

( * ) Notice: Subject to any disclaimer, the term of this patent is extended or adjusted under 35 U.S.C. 154(b) by 332 days.

(21) Appl. No.: 11/959,984

(22) Filed: Dec. 19, 2007

(65) Prior Publication Data

US 2008/0188694 A1 Aug. 7, 2008

Related U.S. Application Data

(60) Provisional application No. 60/872,422, filed on Dec. 29, 2006.

(51) Int. Cl.
*C07C 37/08* (2006.01)
*C07C 27/00* (2006.01)
*C07C 45/53* (2006.01)
*C07C 1/24* (2006.01)
*C07C 407/00* (2006.01)

(52) U.S. Cl. ............... 568/798; 568/385; 568/568; 568/815; 585/435

(58) Field of Classification Search ........... 568/798
See application file for complete search history.

(56) References Cited

U.S. PATENT DOCUMENTS

| | | | | |
|---|---|---|---|---|
| 3,308,069 A | | 3/1967 | Wadlinger et al. ........ 252/455 |
| 4,358,618 A | | 11/1982 | Sifniades et al. ........ 568/385 |
| 4,440,871 A | | 4/1984 | Lok et al. ................ 502/214 |
| 4,490,565 A | | 12/1984 | Chang et al. ........... 568/798 |
| 4,490,566 A | | 12/1984 | Chang et al. ........... 568/798 |
| 5,126,308 A | | 6/1992 | Barger et al. ........... 502/214 |
| 5,191,124 A | | 3/1993 | Schwalm et al. ........ 568/18 |
| 5,723,710 A | | 3/1998 | Gajda et al. ............ 585/467 |
| 6,169,216 B1 * | | 1/2001 | Levin et al. ............ 568/798 |
| 6,201,157 B1 | | 3/2001 | Keenan ................. 568/798 |
| 6,307,112 B1 | | 10/2001 | Weber et al. .......... 568/798 |
| 6,419,895 B1 | | 7/2002 | Lewis et al. .......... 423/718 |
| 6,444,861 B1 * | | 9/2002 | Tanger et al. ......... 568/798 |
| 6,613,302 B1 | | 9/2003 | Moscoso et al. ...... 423/718 |
| 6,677,490 B2 * | | 1/2004 | Clark et al. ........... 568/344 |
| 6,710,003 B2 | | 3/2004 | Jan et al. ............... 502/60 |
| 6,756,030 B1 | | 6/2004 | Rohde et al. .......... 423/718 |
| 6,776,975 B2 | | 8/2004 | Wilson et al. ......... 423/713 |
| 6,872,866 B1 | | 3/2005 | Nemeth et al. ........ 585/481 |
| 7,141,700 B1 * | | 11/2006 | Schmidt et al. ....... 568/385 |
| 7,417,003 B2 * | | 8/2008 | Schmidt et al. ....... 502/63 |
| 2002/0049132 A1* | | 4/2002 | Jan et al. ............... 502/60 |

FOREIGN PATENT DOCUMENTS

EP  0 492 807 A2  11/1991
WO  WO 00/29107  5/2000

OTHER PUBLICATIONS

Sasidharan et al., 52 J. Chem. Res., 52-53 (1997).*
Journal of the American Chemical Society (1979), 101:21, p. 6439-6441.*
M. Misono et al., "Hydroisomerization of n-hexane and n-heptane over platinum-promoted $Cs_{2.5}H_{0.5}PW_{12}O_{40}$ (Cs2.5) studied in comparison with several other solid acids", Topics in Catalysis 11/12, (2000), pp. 239-246.
H. van Bekkum et al., "Thermoporometry as a new tool in analyzing mesoporous MCM-41 materials", Catalysis Letters 33, (1995), pp. 145-156.
H. van Bekkum et al., "MCM-41 type materials with low Si/Al ratios", Catalysis Letters 33 (1995), pp. 157-163.
Z. Olejniczak, "Heterogenization of 12-tungstophosphoric acid on stabilized zeolite Y", Topics in Catalysis 11/12 (2000), pp. 391-400.

* cited by examiner

*Primary Examiner*—Brian J Davis
(74) *Attorney, Agent, or Firm*—David J Piasecki

(57) ABSTRACT

The present invention provides a process for decomposing a cumene hydroperoxide to produce phenol and acetone. The process utilizes a solid catalyst that can be non-layered or layered. The process includes: (1) introducing a process stream containing cumene hydroperoxide into a reaction vessel; (2) contacting the process stream with catalyst particles to form a process stream; and (3) withdrawing a portion of the product stream from the reactor and recovering phenol and acetone products.

20 Claims, 3 Drawing Sheets

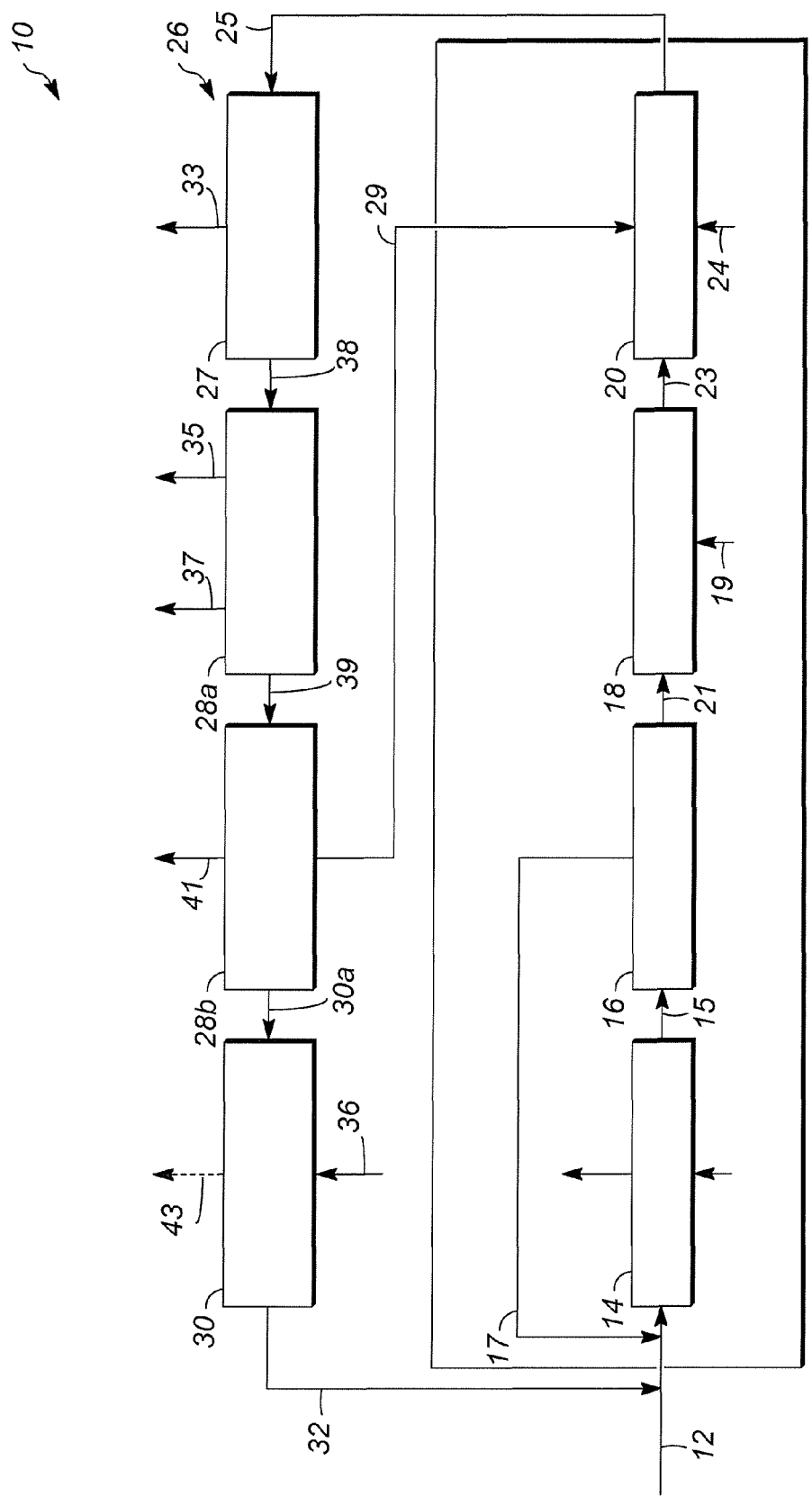
FIG. 1 -- Prior Art --

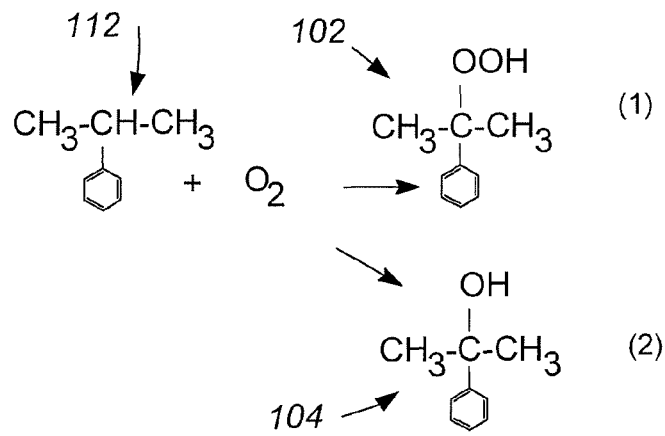
-- Prior Art --   FIG. 2
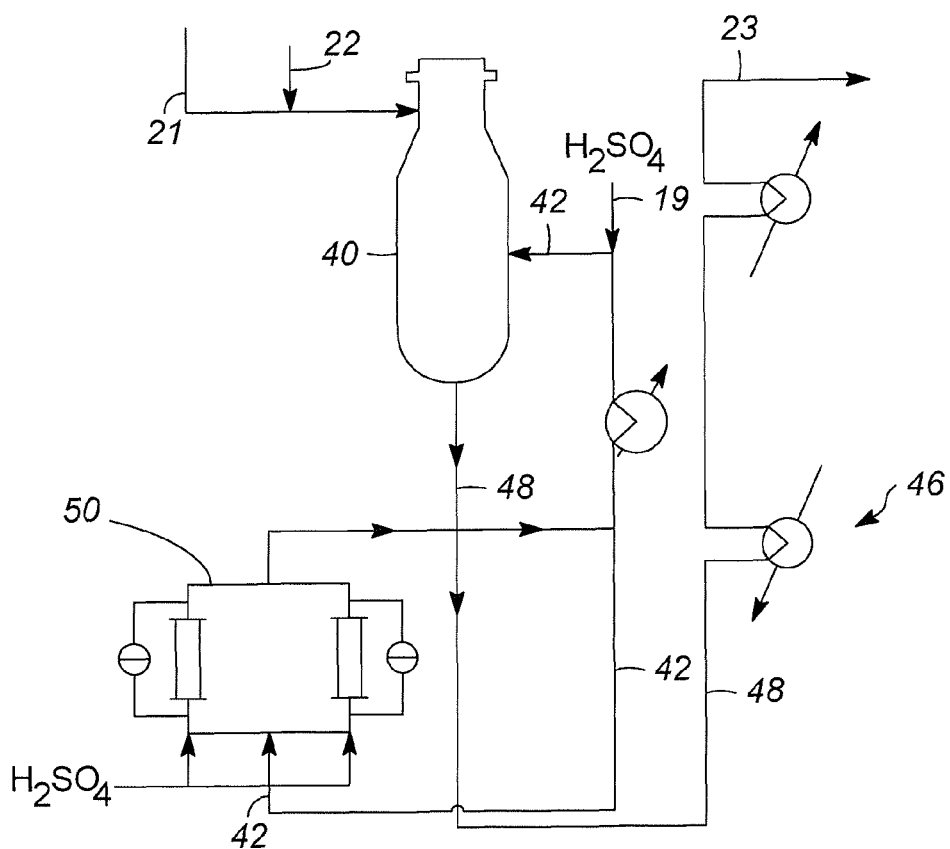
-- Prior Art --   FIG. 3

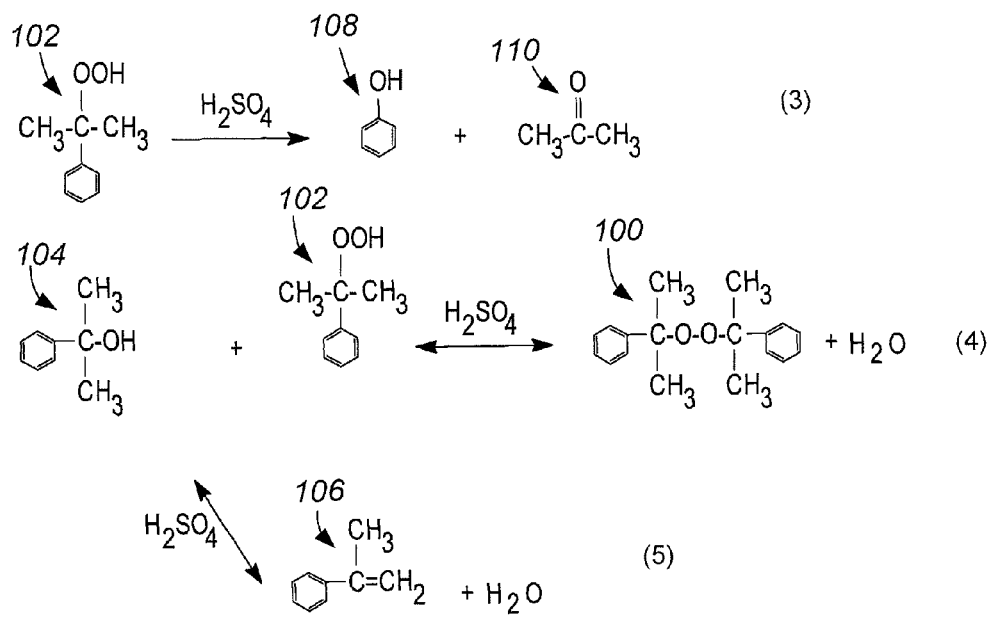
-- Prior Art --  FIG. 4
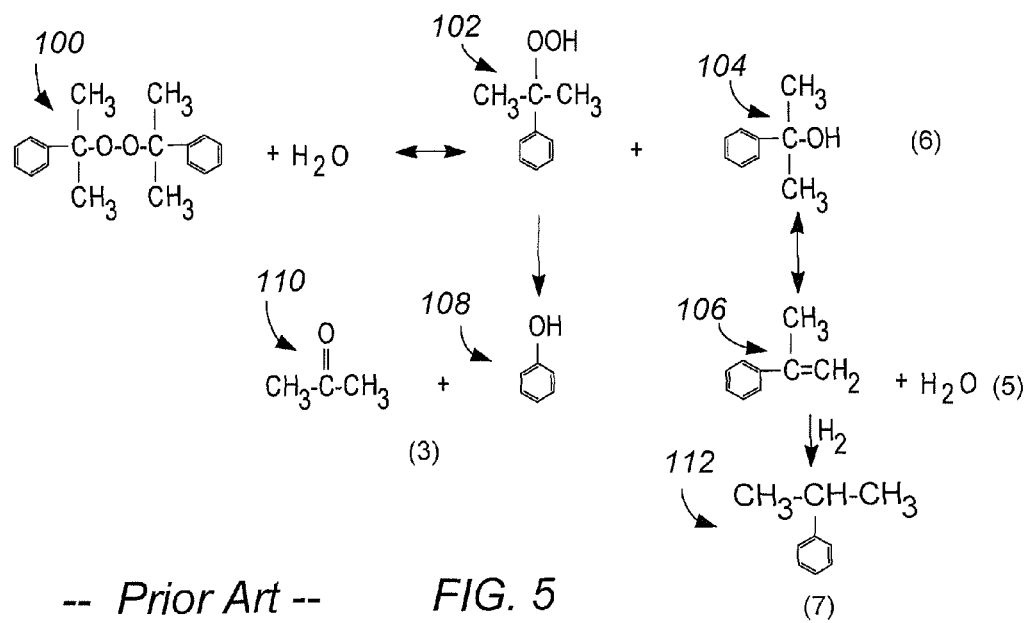
-- Prior Art --  FIG. 5

SOLID ACID CATALYST AND PROCESS FOR DECOMPOSITION OF CUMENE HYDROPEROXIDE

CROSS-REFERENCE TO RELATED APPLICATION

This application claims priority from Provisional Application Ser. No. 60/872,422 filed on Dec. 29, 2006, the contents of which are hereby incorporated by reference.

BACKGROUND OF THE INVENTION

The current process of choice for commercial phenol production utilizes the autocatalytic cumene/air oxidation to cumene hydroperoxide (CHP) route for over 50% of the world's production of phenol. A key step in this process is the decomposition (cleavage) of CHP produced in the oxidation section of the plant to phenol and acetone using dilute mineral acid ($H_2SO_4$) as an acid catalyst. Use of the liquid acid requires subsequent neutralization and purification of the phenol at substantial cost, and a waste stream generation that could be avoided if an effective solid acid catalyst could be used. CHP decomposition is a very exothermic reaction which is normally carried out on a commercial scale in continuous stirred or back-mixed reactors. In such reactors only a small fraction of CHP is unreacted at any given time and the reaction medium consists essentially of the products of decomposition of CHP, i.e., phenol and acetone, plus any solvent (e.g., cumene and/or recycle acetone) and other materials added with CHP to the reactor. During cumene oxidation small amounts of dimethylphenylcarbinol (DMPC) and acetophenone are also formed. In the presence of acid catalyst, DMPC dehydrates to alpha-methylstyrene (AMS), a useful by-product. Very high yields of AMS can be obtained from pure DMPC, e.g., 98% yield upon dehydration over acidic silica at 300° C. In the presence of phenol, however, and more specifically in a phenol/acetone/cumene mixture which is a solvent in the decomposition of CHP/DMPC mixtures, the ultimate AMS yield is normally about 50-60 mol % of the DMPC. Main by-products are AMS dimers and cumylphenol which have no commercial value. Formation of cumylphenol also reduces the phenol yield.

Although phenol and acetone have been produced by the decomposition of the cumene oxidation product for decades using a liquid mineral acid such as sulfuric acid as a catalyst, there is a continuing incentive to produce them at a lower cost and with a reduced by-product formation.

INFORMATION DISCLOSURE

U.S. Pat. No. 4,358,618 (Sifniades et al.) discloses a multistep process for the production of acetone and phenol by the decomposition of cumene hydroperoxide.

U.S. Pat. No. 6,201,157 B1 (Keenan) discloses a process for the decomposition of cumene hydroperoxide using an acid catalyst and neutralizing the acid catalyst after the completion of the decomposition by the addition of an amine.

U.S. Pat. No. 6,307,112 (Weber et al.) discloses a process for cleaving cumene hydroperoxide wherein the mass flow ratio of a recycled partial product stream to the cumene hydroperoxide-containing feed stream sent to the cleavage reactor is less than 10. The patent discloses the use of vertical tube bundle heat exchangers.

U.S. Pat. No. 4,490,565 and U.S. Pat. No. 4,490,566 (Chang) disclose the production of phenol and acetone by the cleavage of cumene hydroperoxide in the presence of a solid heterogenous catalyst with acidic activity including, respectively, zeolite beta and ZSM-5.

European Patent Application Publication No. 0 492 807 A2 (Knifton) discloses the production of phenol and acetone by the cleavage of cumene hydroperoxide in the presence of a solid catalyst with acidic activity including the isostructural group of faujasite and zeolites X and Y.

U.S. Pat. No. 6,710,003 (Jan et al.) discloses the process for preparing attrition resistant zeolitic layered catalyst compositions.

BRIEF SUMMARY OF THE INVENTION

The present invention provides a process for decomposing a cumene hydroperoxide to produce phenol and acetone using either layered catalyst particles or non-layered catalyst particles. The process includes: (1) introducing a process stream containing cumene hydroperoxide into a reaction vessel; (2) contacting the process stream with catalyst particles to form a product stream, the catalyst particles having an inner core, an outer layer of an acidic material bonded to the inner core; and (3) withdrawing a portion of the product stream from the reactor and recovering phenol and acetone products.

The present invention further provides a process for decomposing a cumene hydroperoxide to produce phenol and acetone. The process includes: (1) introducing a process stream containing cumene hydroperoxide into a reaction vessel; (2) contacting the process stream with catalyst particles to form a product stream, the catalyst particles having an inner core, an outer layer bonded to the inner core, the outer layer comprising an acidic material having volumetric fractions of 0.17 to 0.62 of the entire catalyst particle; and (4) withdrawing a portion of the product stream from the reactor and recovering phenol and acetone products.

The present invention further provides a process for decomposing a cumene hydroperoxide to produce phenol and acetone. The process includes: (1) introducing a process stream containing cumene hydroperoxide into a reaction vessel; (2) contacting the process stream with catalyst particles to form a product stream, the catalyst particles of a material selected from the group consisting of BEA, MWW, UZM-4, UZM-5, UZM-8, MOR, MEI, MTW, SPA (Solid Phosphoric Acid) and Cs salts of heteropoly acid; and (3) withdrawing a portion of the product stream from the reactor and recovering phenol and acetone products.

BRIEF DESCRIPTION OF THE DRAWINGS

FIG. 1 provides a block flow diagram of a prior art process that utilizes the cumene peroxidation route to produce phenol.

FIG. 2 shows the main reactions that occurs during the oxidation and decomposition steps of the prior art process.

FIG. 3 shows a flow diagram for the decomposition section of the prior art process.

FIGS. 4 and 5 show the reactions occurring during the dehydration step of the prior art process that follows the main decomposer reactor to convert major side products such as DCP and DMPC to additional CHP and AMS respectively for recycle to phenol.

DETAILED DESCRIPTION OF THE INVENTION

FIG. 1 shows a block flow diagram 10 of a prior art process that utilizes the cumene peroxidation route to produce phenol and acetone. The chemical reactions that occur in this process are set forth in FIGS. 2, 4, and 5. FIG. 2 shows Reactions (1) and (2) in which cumene 112 is oxidized to form cumene hydroperoxide (CHP) 102 or dimethylphenylcarbinol (DMPC) 104. In FIG. 3, CHP 102 is then reacted in the presence of a liquid mineral acid such as sulfuric acid to form phenol 108 and acetone 110 in Reaction (3). FIG. 4 shows two competing side reactions that can occur. In Reaction (4), dimethylphenylcarbinol (DMPC) 104 from Reaction 2 reacts with CHP 102 to form dicumylperoxide (DCP) 100. In a Reaction (5) DMPC 104 is dehydrated in the presence of sulphuric acid to form alpha-methylstyrene 106. FIG. 5 shows a Reaction (6) where the DCP 100 is hydrated to form CHP 102 and DMPC 104. The CHP 102 can then be used to form phenol 108 and acetone 110 which is Reaction (3) from FIG. 4. The DMPC 104 can be dehydrated to form AMS 106 which is Reaction (5) from FIG. 4. AMS 106 can be hydrogenated to form cumene 112 in Reaction (7) and the cumene 112 can then be recycled to form acetone 110 and phenol 108.

FIG. 1 shows a flow scheme of where the reactions set forth in FIGS. 2, 4 and 5 are carried out. First, a supply stream of cumene 12 is provided under pressure to an oxidation station 14 where cumene is first oxidized in air to form CHP at very high yield with cumene conversion in the range of about 20 to 42% per-pass. No catalyst is used for this step in the process other than the CHP itself which is autocatalytic and does not require (and is highly undesirable) to have other acids present in the reactor. A portion of the effluent from the oxidation station 14 is transferred through line 15 to a concentration station 16 where the CHP concentration is raised to a level of about 80 to 85 wt %. A portion of uncoverted cumene is recycled through line 17 back to the supply line 12 and is fed again through the oxidation station 14.

The concentrated CHP is transferred through line 21 from the concentration section 16 to a decomposition (e.g., cleavage) station 18 where the CHP is catalytically decomposed using dilute mineral acid (e.g., $H_2SO_4$) supplied through line 19 to phenol and acetone under very carefully controlled temperature, acid concentration, water, and residence time to ensure that essentially complete conversion of CHP occurs. Failure to achieve complete conversion of CHP to phenol and acetone risks the build up of the CHP to a level which can be explosive in nature. Thus this section is very critical for safety, reliability, and overall yield performance standpoint.

The effluent from the decomposition station 18 is transferred through line 23 to a neutralization station 20 where the decomposition station effluent is contacted with a neutralizing agent provided through line 24. The neutralizing agent typically is 2-methylpentamethylenediamine (Dytek), hexamethylenediamine, triethylenetetramine, or diethylenetriamine.

Upon sufficient neutralization an effluent is delivered from the neutralization station 20 to a product recovery and purification station 26 via line 25 where acetone is recovered in station 27, and is transferred from the station through line 33. Effluent from station 27 is transferred through line 38 and purified in station 28*a* where residue is removed through line 35 and some purified phenol is recovered through line 37. Remaining effluent from station 28*a* is conveyed through line 39 to a phenol recovery 28*b* where a first portion of the recovered phenol is conveyed through line 41 to storage or for immediate use and a second portion is recirculated through line 29 back to the neutralization station 20. A second effluent containing AMS from station 28*b* is directed through line 30*a* to station 30 where a portion of the AMS is hydrogenated with hydrogen from line 36 back to cumene and the cumene is transferred from the AMS station 30 through recycle line 32 back to mix with the cumene feed line 12 and passed again through the connected stations. It may be also desirable to recover a portion of AMS through line 43.

FIG. 3 shows a flow diagram for the decomposition station or section 18 of the plant. The decomposition section 18 is where a process shown in FIG. 4 is carried out. The decomposition station 18 has a decomposer vessel 40 where CHP in line 21 optionally supplemented with water in line 22 is converted to phenol and acetone at about 60° C. to 70° C. using about 20 to 60 ppm liquid $H_2SO_4$ as a catalyst supplied through lines 19. Calorimeter 50 monitors conversion to maintain the concentration of $H_2SO_4$ at an appropriate level to maintain conversion. A high recycle ratio (e.g., 5/1 to 100/1) of decomposer effluent to feed through a decomposer loop 42 is used to control heat and ensure conversion from about 85 wt % CHP down to about 1 to 2.5 wt % CHP.

A dehydrator 46 receives a portion of the effluent from the decomposer through line 48 where DCP (dicumylperoxide) is converted to CHP and DMPC (dimethylphenylcarbinol) and DMPC is subsequently dehydrated to form AMS (alpha-methylstyrene) in high yield (see FIGS. 4 and 5). This later step allows AMS to be hydrogenated back to cumene and recycled in the process to reduce the fresh cumene feed consumption. Line 23 takes the effluent to the neutralization station 20.

The present invention provides a process for decomposing CHP without the use of $H_2SO_4$, or other liquid mineral acid, as a catalyst. The decomposition of CHP is catalyzed by a solid acid catalyst, including non-layered and layered catalyst particles. Suitable materials for non-layered catalyst include FAU, BEA, MWW, UZM-4, UZM-5, UZM-8, MOR, MEI, MTW, SPA and cesium (Cs) salts of heteropoly acid. FAU, BEA, MWW, BPH, UFI, MOR, MEI, MTW are 3-letter codes representing the framework types and are assigned by Structural Commission of International Zeolite Association.

BEA or zeolite beta is a microporous alumino-silicate that has three intersecting 12-ring channels and was synthesized as per U.S. Pat. No. 5,723,710.

UZM-4 is a crystalline alumino-silicate that has BPH morphology and is structurally related to zeolite Q and is as described in U.S. Pat. No. 6,419,895. UZM-4M is a modified form of UZM-4 using a process described in U.S. Pat. No. 6,776,975. The modification process improves the stability of the catalyst and optimizes its acidity, to render UZM-4M thermally and hydrothermally stable to render the catalyst suitable for various catalytic applications.

UZM-5 is a crystalline alumino-silicate that has UFI structure and its structure and method of synthesis is set forth in U.S. Pat. No. 6,613,302.

UZM-8 is a crystalline zeolite containing a layered framework of aluminum oxide and silicon dioxide tetrahedral units. The structure and method of synthesizing UZM-8 is disclosed in U.S. Pat. No. 6,756,030.

Mordenite is a crystalline zeolite having one 12-ring channel with two intersecting 8-R channels.

MTW is a microporous alumino-silicate that has one 12-ring channel. The structure of MTW and its method of synthesis is disclosed in U.S. Pat. No. 6,872,866. In one preferred form of the invention, the MTW had a silica to alumina ratios ranging from 20 to 45.

Solid phosphoric acid (SPA) is phosphoric acid supported on silica phosphate and was prepared in accordance with methods well known to those skilled in the art. SPA is commercially available from Innophos Corp. located in Kentucky and Houston, Tex.

The Cesium salts of heteropoly acids were synthesized in accordance with methods known to those of ordinary skill in the art. Salts of heteropoly acids have general formulation of $M1_xH_{3 \ or \ 4-x}M2M3_{12}O_{40}$ where M1 is alkali metal and M2 is P or S1 and M3 are Group VI transition metals (Cr, Mo and W) as described in "Heteropoly and Isopoly Oxometalates"

by Michael Pope. They can be used as is or supported on amorphous or mesoporous crystalline materials such as MCM-41 as exemplified in M. Misono et. al. in Topics in Catalysis, 2000, by H. van Bekkum et. al. in Catalysis Letter 1995 and by Z. Olejniczak in also Topics in Catalysis of 2000.

In one preferred form of the invention, it is believed that the use of a layered catalyst particle may limit the reaction path, and thereby minimize the undesirable products and thus enhance the selectivity and stability. The CHP decomposition is extremely fast, diffusionally limited, and prone to formation of heavy condensed oxygenated by-products which tend to condense further if not desorbed from the surface of the catalyst very quickly.

In one preferred form of the invention, the layered catalyst has an inner core and an outer layer comprising an acidic zeolitic or non-zeolitic molecular sieve and binder, and having volumetric fractions of the entire catalyst particle, in a preferred form of the invention from about 0.17 to about 0.62, more preferably from about 0.235 to about 0.503 and most preferably from about 0.289 to about 0.503. The inner core and outer layer form a generally, but not limited to, spherical particle having an average diameter of from about 0.1 mm to about 5.5 mm, preferably from about 0.7 mm to about 3 mm.

Examples of materials suited for the outer layer include those that are acidic, more preferably those materials having an acidity level when measured by $NH_3$-TPD of equal to or greater than about 0.36 minimum mmoles $NH_3$ per gram catalyst at 150 to 550° C. based on using a powder form of the outer layer material. Separate and apart from the $NH_3$-TPD acidity level, it has also been determined that the minimum acidity level can be quantified using a pyridine IR method of determining Brønsted acidity at 150° C. to be equal to or greater than about 0.1 minimum AU/mg catalyst for the powder form of the catalyst material of the outer layer.

The procedure for determining the $NH_3$TPD acidity and pyridine IR acidity is described as follows:

$NH_3$-TPD Experimental Procedure

Calibrate $NH_3$-TPD system with 5 injections of 0.2 cc pulses of $NH_3$ at 2 minute intervals into a flow of UHP grade helium at 40 cc/minute. The data collected from the Thermal Conductivity Detector is integrated and used to calibrate the detector response to a known quantity of $NH_3$. Weigh approximately 250 mg of equilibrated (for moisture content) sample and place in the reactor. The sample is pretreated in a flow of 20% $O_2$/He UHP grade at a rate of 100 cc/minute and with a temperature ramp of 10° C./minute up to a maximum temperature of 650° C. The sample is held at this temperature for one hour, then purged with UHP grade helium for 15 minutes and cooled to the saturation temperature. The pretreatment is for removal of water and residual contaminants. Saturate with anhydrous $NH_3$ at 150° C. using multiple pulses of $NH_3$ injected into He flowing at 40 cc/min. The minimum quantity of $NH_3$ used to saturate the sample is 50 cc. The excess ammonia is purged from the sample in flowing (40 cc/min) UHP grade helium for ~8 hours. The $NH_3$ is desorbed from the sample in a flow (40 cc/min) of UHP grade helium with a temperature ramp of 10° C./minute to a final temperature of 650° C. All gases have been purified using appropriate gas purifiers. The $NH_3$ desorbed is detected with a Thermal Conductivity Detector. The detector response is converted to moles of $NH_3$ using the detector response obtained at the beginning of the experiment. The integrated results are reported by integration of the temperature range of interest and reported as mmoles $NH_3$/g sample.

Pyridine-Infrared Experimental Procedure

The samples are ground to a fine powder using an agate mortar and pestle. 10-15 mg of the ground powder sample is typically pressed at 5000 psig to form a 13-mm self-supporting pellet. The samples pressed into pellets are heated to 500° C. in a flow of Helium for 2 hours. At the end of the heating cycle the sample is cooled to ambient temperature in Helium and a spectrum is collected for hydroxyl analysis. Helium gas saturated with pyridine at 7° C. is equilibrated with the sample at 150° C. for one hour. At the end of the adsorption cycle, the excess gas phase pyridine is purged off and the sample is cooled to room temperature. Discrete desorption experiments are conducted at 150°, 300° and 450° C. for 60 minutes each. A spectrum is recorded after cooling to room temperature following each desorption step. The spectra are recorded on a Nicolet Magna 550 Infrared spectrometer at 2 $cm^{-1}$ resolution, using a cooled MCT detector. The data analysis is performed using GRAMS AI software system from Thermo Scientific and Microsoft Excel.

For layered catalyst particles, the following materials have been found to be suitable for the outer layer of acidic material and include, but are not limited to, zeolite beta, FAU, MWW, UZM-4/BPH, UZM-5/IFI, UZM-8, ZSM-18/MEI, MOR, MTW, SPA and Cs salts of heteropoly acid. Zeolite beta is especially preferred and is described in U.S. Pat. No. 3,308,069 according to its structure, composition, and preferred methods of synthesis. The other examples of zeolites that can be used are those having known structure types, as classified according to their three-letter designation by the Structure Commission of the International Zeolite Association. Zeolite UZM-8 is defined in U.S. Pat. No. 6,756,030, which provides information on its unique structure as well as its synthesis details. Further, it is also possible to layer non-zeolitic materials such as hetero-poly acid and preferably insoluble cation exchanged hetero-poly acid. The use of insoluble cation exchanged hetero-poly acid in acid-catalyzed reactions is illustrated in WO 00/29107 and the references cited therein by Wang et al.

It may also be desirable to effectively vary the morphology of acidic material as in the use of UZM-5, UZM-8, SPA and MTW or selective cation exchanged zeolitic and non-zeolitic molecular sieves that promote activity on the external surface of the zeolite crystallites found on the structures. Alternatively, strong zeolites such as beta or UZM-4 zeolite with open, three dimensional pore structures, if used sparingly in a layered sphere composite, may also allow ready access to the acid sites with fast desorption of heavy products to avoid deactivation. The shape selectivity of beta zeolite, for example, may prevent heavy condensed products from forming altogether as such materials are not easily accommodated in the pore structure due to steric constraint. Additionally, optimizing the Si/Al ratio of the zeolite will be necessary to achieve the acidity strength and density needed to maximize catalytic activity and selectivity. The Si/Al ratios used for the zeolite examples shown herein are representative of those typically observed and are not necessarily limited to these values as further optimization of this property can be used to further enhance the activity and selectivity in both the layered and unlayered catalyst process.

The inner core material is selected from, for example, refractory inorganic oxides, silicon carbide and metals. Examples of refractory inorganic oxides include without limitation alpha alumina, gamma alumina, theta alumina, chi alumina, cordierite, zirconia, titania and mixtures thereof. Preferred inorganic oxides include alpha alumina, gamma alumina, chi alumina and cordierite.

The materials that form the inner core can be formed into a variety of shapes such as pellets, extrudates, spheres, rings, trilobes, saddles, or other physical forms known in the art. Of course, not all materials can be formed into each shape. Preparation of the inner core can be done by means known in the art such as oil dropping, pressure molding, metal forming, pelletizing, granulation, extrusion, rolling methods and marumerizing. A spherical inner core is commonly used, although pressure drop considerations can warrant the use of shaped particles that result in a higher void fraction when such shapes are packed into a catalyst bed. The inner core whether spherical or not has an effective diameter of about 0.05 mm to about 5 mm and preferably from about 0.4 mm to about 3 mm. For a non-spherical inner core, effective diameter is defined as the diameter the shaped particle would have if it were molded into a sphere. Once the inner core is prepared, it is calcined at a temperature of about 400° C. to about 1500° C.

The inner core is now coated with the acidic outer layer described above by forming a slurry of a powder of the outer layer material and then coating the inner core with the slurry by means well known in the art. To form a layered composition in which the outer layer is a zeolite bound with an inorganic metal oxide, the slurry will contain an appropriate sol, or carrier material, of the binder used for suspending the zeolite. In the case of incorporating alumina, silica, magnesia, zirconia or titania binders into the zeolite for producing the outer layer of the composition, it is appropriate to use a hydrosol. For example, any of the aluminas can be mixed with water and an acid such as nitric, hydrochloric, or sulfuric to give an aluminum sol. Alternatively, an aluminum sol can be made by for example, dissolving aluminum metal in hydrochloric acid and then mixing the aluminum sol with the alumina powder. When the alumina powder is desired, it is also possible to use a solution of boehmite or aluminum nitrate in place of the aluminum sol.

Types of silica sols used to form a silica bound zeolite are commercially available as aquasols or organosols containing dispersed colloidal silica particles. Otherwise, a silica gel may be used to ultimately form a silica binder in the zeolitic outer layer. If a magnesia binder is desired, the starting slurry will contain hydrolyzed magnesium alkoxide. When a zirconia binder is used for the outer layer preparation, the preferred starting acidic sol is an aqueous zirconium acetate solution, which is preferably combined with an urea gelling agent. When a titania binder is used, the acidic sol is preferably a solution of titanyl oxychloride, which is also preferably combined with an urea gelling agent. The amount of sol added to the slurry is based on typical binder contribution from about 10% to about 50% of the weight of the bound zeolite forming the outer layer of the composition. Those skilled in the art will readily appreciate the relationship between the zeolite:sol weight ratio of the slurry and the concentration of binder in the resulting outer layer.

In one preferred form of the invention, the slurry will contain an organic bonding agent that: 1) aids in the adhesion of the outer layer material (i.e. the bound zeolite) to the inner core; and 2) improves the overall strength of the outer layer zeolite/binder system. Examples of this organic bonding agent include, but are not limited to, polyvinyl alcohol (PVA), hydroxylpropyl cellulose, methyl cellulose and carboxy methyl cellulose. The amount of organic bonding agent which is added to the slurry will vary considerably from about 0.1% to about 5% by weight of the slurry. How strongly the outer layer is bonded to the inner core can be measured by the amount of layer material lost during an attrition test, i.e., attrition loss. Loss of the zeolitic outer layer by attrition is measured by agitating the catalyst, collecting the fines and calculating an attrition loss. It has been found that by using an organic bonding agent as described above, the attrition loss is less than about 25% by weight of the outer layer. In most cases, this attrition loss is less than 10%. Physical strength of the catalyst particles is critical in the proposed CHP decomposition process where the solid catalyst particles are introduced to the decomposer as a slurry, colloidal mixture or otherwise suspended solid/liquid mixture.

Depending on the particle size of the zeolite employed in the outer layer, it may be necessary to mill the slurry in order to reduce the particle size and simultaneously give a narrower particle size distribution. This can be done by means known in the art such as ball milling for times of about 30 minutes to about 5 hours and preferably from about 1.5 hours to about 3 hours. It is believed that using a slurry with a particle size distribution that has been adjusted in this manner improves the bonding of the outer layer to the inner core. It should be also noted that, in addition to the zeolitic powder, sol of the binder, and bonding agent, the slurry will contain a balance of de-ionized water. The amount of water is often adjusted after any milling operation in order to obtain a viscosity of the slurry in the range from about 30 to about 600 centipoise.

Without wishing to be constrained by any particular theory, it is believed that the organic bonding agent aids in providing a high-density, mechanically-superior zeolite/binder system that is used to form the outer layer. Furthermore, it appears that bonding agents such as PVA aid in making an interlocking bond between the outer layer material and the inner core. Whether this occurs by the PVA reducing the surface tension of the core or by some other mechanism is not clear. What is clear is that a considerable reduction in loss of the outer layer by attrition is observed with the use of a bonding agent. This desirable characteristic, therefore, results from a combination of a structurally improved zeolite/binder system as well as an enhanced bond between the outer layer and inner core, both of which are attributable to the use of the organic bonding agent.

Coating of the inner core with the slurry can be accomplished by means such as rolling, dipping, spraying, etc. to yield a coated core having an outer layer. One preferred coating technique involves using a fixed fluidized bed of inner core particles and spraying the slurry into the bed to coat the particles evenly. The thickness of the layer of the coated core can vary considerably, but usually, in a preferred form of the invention is an outer layer having volumetric ratios of from about 0.17 to about 0.62 of the entire catalyst particle, more preferably from about 0.235 to about 0.503 and most preferably from about 0.289 to about 0.503. It should be pointed out that the optimum layer thickness will depend on the specific process design of the decomposition section of the unit.

Once the inner core is coated with the outer bound zeolite layer, the resultant coated core is dried at a temperature of about 50° C. to about 300° C. for a time of about 1 hour to about 24 hours to provide a dried coated core. Subsequently, the dried coated core is calcined at a temperature of about 400° C. to about 900° C. for a time of about 0.5 hour to about 10 hours to effectively bond the outer layer to the inner core and provide the layered catalyst particle of the present invention. The calcination step also removes any remaining organic template material within the zeolite as well as any residual bonding agent. In some cases, the catalyst may be activated in a modified calcination step wherein the organic template is first decomposed in a flow of pure nitrogen. The oxygen concentration is then gradually increased to combust any residual hydrocarbons in the zeolite. It is also possible to combine the drying and calcining operations into a single step.

The following examples are presented in illustration of this invention and are not intended as undue limitations on the generally broad scope of the invention as set forth in the appended claims.

Example 1

The preparations of zeolite beta layered catalysts of different thicknesses on inner cores of varying diameters for testing in Runs 1 through 12 followed procedures described in U.S. Pat. No. 6,710,003 and more particularly included the following steps.

A solution of polyvinyl alcohol (PVA) bonding agent (20% by weight), aluminum sol (20% by weight) and de-ionized water (balance) was prepared and mixed for 15 minutes. A pre-weighed amount of zeolite beta powder was blended into this solution and the resulting slurry was stirred for 15 minutes. The amount of zeolite beta used was based on obtaining a final outer layer comprising 70% by weight zeolite and 30% by weight alumina binder, resulting from the incorporation of aluminum sol. A more uniform composition was obtained by ball milling the slurry for two hours, after which the viscosity was adjusted to about 100 centipoise by adding a further amount of de-ionized water.

A fixed fluidized bed of gamma alumina particles having an average diameter of about 1.6 mm were then sprayed with the slurry to provide an even coating. After the coating step, the material was dried at a temperature of 100° C., and thereafter at 350° C. for one hour and at 630° C. for two hours in flowing air prior to use in CHP decomposition tests. The calcination serves to remove remaining organic template and PVA, as well as to convert the alumina sol into gamma alumina. The resulting catalysts particles had an outer layer having volumetric ratios of about 0.16 to about 0.63 and thickness of from about 37 μm to about 240 μm and as shown in Table 1 below. Very good layer physical strength, as determined by subjecting the resulting layered composition to an attrition test, was achieved using this preparation method. A relative attrition value of 1.3 was observed.

Example 2

SAPO-11 layered catalysts were prepared also on gamma alumina spheres of about 1.6 mm diameter as described in the following for the catalyst tested in Runs 15 to 18 as shown in Table 1 below.

SAPO-11 was synthesized as per procedures described in U.S. Pat. Nos. 4,440,871, 5,126,308 and 5,191,124. A solution of polyvinyl alcohol (PVA) bonding agent (40% by weight), aluminum sol (20% by weight) and de-ionized water (balance) was prepared and mixed for 15 minutes. A pre-weighed amount of SAPO-11 powder was blended into this solution and the resulting slurry was stirred for 15 minutes. The amount of SAPO-11 powder used was based on obtaining a final outer layer comprising 70% by weight zeolite and 30% by weight alumina binder, resulting from the incorporation of aluminum sol. A more uniform composition was obtained by ball milling the slurry for two hours, after which the viscosity was adjusted to about 100 centipoise by adding a further amount of de-ionized water.

A fixed fluidized bed of gamma alumina particles having an average diameter of about 1.6 mm were then sprayed with the slurry to provide an even coating. After the coating step, the material was dried at a temperature of 100° C., and thereafter at 630° C. for two hours in flowing air prior to use in CHP decomposition tests. The calcination serves to remove remaining organic template and PVA as well as to convert the alumina sol into gamma alumina. The resulting catalyst had an outer layer thickness of approximately 32 μm to 154 μm as shown in Table 1 below and a relative attrition value of 0.4.

The catalyst particles described herein can be used to replace the liquid mineral acid used to catalyze the CHP decomposition reaction to phenol 108 and acetone 110 shown in FIG. 3 and carried out in the decomposition station 18 of the plant 10. The decomposer vessel 40 and the liquid acid supply line 19 in FIG. 3 can be replaced by a fixed bed reactor system such as a fixed liquid fluidized bed of solid catalyst, a slurry reactor, a transport liquid riser type reactor, an ebuliated bed reactor, or other such reactors that can operate in the liquid phase. In one preferred form of the invention the catalyst can be supplied to the decomposer 40 or to another appropriate vessel, by introducing the solid catalyst particles in a slurry, colloidal mixture, or otherwise suspended liquid/solid mixture. The present invention also contemplates, instead of replacing the decomposer vessel 40, reconfiguring an existing decomposer vessel 40 to achieve a fluidized bed or ebuliated bed of catalyst in the decomposer vessel 40.

Example 3

In Runs 1 to 18, the catalyst samples made in accordance with Examples 1 and 2 and having outer layers of varying thicknesses, set forth in Table 1 below, were screened for activity and selectivity. Runs 1-12 utilized a zeolite beta outer layer having a thickness specified in Table 1. Runs 13-16 and 18 utilized a SAPO-11 outer layer having a thickness specified in Table 1. Run 17 utilized an SM-3 outer layer having the thickness specified Table 1. The catalysts were tested using the following experimental set up. Approximately 4 gms of catalyst were added to 36 cc of a 1:1 molar mixture of acetone/phenol in a 50 cc stirred glass vessel operating as a continuous stirred tank reactor (CSTR) system to simulate the environment of a commercial decomposer reactor. The temperature of the mixture is then raised to about 55° C. to 70° C. and approximately 4 gms of an 85 wt % CHP concentrate solution derived from a commercial phenol unit (see reference numeral 21 of FIG. 1) as a source of fresh CHP feed is injected into the reaction mixture in about 30 seconds. Reaction products and temperature were monitored during the course of the runs to determine the extent of reaction and the product selectivity over an approximately 25 min of total reaction time. A continuous circulation of the reaction products was maintained throughout the course of the run to control the strong exothermic heat of reaction that occurs and to simulate CSTR reactor conditions. Results obtained are described as followed with detailed catalysts and product yields and selectivities shown in the Table 1 at a reaction time of 25 minutes.

TABLE 1

| Run # | CORE Material | Diameter (μm) | OUTER LAYER Material | Thickness (μm) | Volume Fraction | Residual CHP (%) t = 25 min | AMS Yield (%) | AMS Selectivity (%) |
|---|---|---|---|---|---|---|---|---|
| 1 | gamma-Al$_2$O$_3$ | 1638 | Beta | 48 | 0.157 | 58.5 | 21.6 | 72.0 |
| 2 | gamma-Al$_2$O$_3$ | 1638 | Beta | 48 | 0.157 | 32.9 | 58.9 | 85.6 |
| 3 | gamma-Al$_2$O$_3$ | 1638 | Beta | 48 | 0.157 | 25.3 | 69.4 | 89.6 |
| 4 | gamma-Al$_2$O$_3$ | 1638 | Beta | 48 | 0.157 | 13.3 | 77.3 | 88.7 |
| 5 | gamma-Al$_2$O$_3$ | 1638 | Beta | 103 | 0.299 | 0.0 | 86.9 | 91.5 |
| 6 | gamma-Al$_2$O$_3$ | 1638 | Beta | 103 | 0.299 | 0.0 | 86.3 | 91.4 |
| 7 | alpha-Al$_2$O$_3$ | 1079 | Beta | 65 | 0.289 | 0.0 | 85.6 | 88.9 |
| 8 | alpha-Al$_2$O$_3$ | 1079 | Beta | 135 | 0.488 | 0.0 | 82.2 | 85.4 |
| 9 | chi-Al$_2$O$_3$ | 1829 | Beta | 165 | 0.392 | 0.0 | 80.9 | 83.6 |
| 10 | chi-Al$_2$O$_3$ | 1839 | Beta | 240 | 0.503 | 0.0 | 82.4 | 86.2 |
| 11 | gamma-Al$_2$O$_3$ | 794 | Beta | 37 | 0.235 | 0.0 | 80.2 | 82.9 |
| 12 | gamma-Al$_2$O$_3$ | 794 | Beta | 157 | 0.632 | 0.0 | 68.5 | 71.4 |
| 13 | gamma-Al$_2$O$_3$ | 1633 | SAPO-11 | 32 | 0.109 | 91.9 | 2.7 | 21.5 |
| 14 | gamma-Al$_2$O$_3$ | 1633 | SAPO-11 | 32 | 0.109 | 92.8 | 2.6 | 25.4 |
| 15 | gamma-Al$_2$O$_3$ | 1633 | SAPO-11 | 154 | 0.404 | 93.3 | 3.7 | 31.1 |
| 16 | gamma-Al$_2$O$_3$ | 1633 | SAPO-11 | 154 | 0.404 | 99.1 | 3.2 | 30.2 |
| 17 | gamma-Al$_2$O$_3$ | 1633 | SM-3 | 55 | 0.178 | 90.6 | 4.4 | 25.1 |
| 18 | gamma-Al$_2$O$_3$ | 1633 | aw SAPO-11 | 51 | 0.166 | 101.8 | 2.5 | 24.1 |

The zeolite beta layered catalysts are active (Runs 1 to 12) for CHP decomposition whereas the layered SAPO-11 and SM-3 catalysts are inactive (Runs 13 to 18) under conditions similar to what is currently being practiced for a state-of-the-art decomposer design (e.g., 55 to 70° C. (131-158° F.) and 25 min residence time using trace sulfuric acid). It has been determined there is a minimum catalyst acidity, as measured by NH$_3$-TPD (See Table 2), needed to catalyze the CHP decomposition reaction. The catalyst acidity should be equal to or greater than 0.36 mmoles NH$_3$ per gram catalyst at 150 to 550° C. based on using a powder form of the outer layer material.

TABLE 2

| CATALYST DESCRIPTION | LETTER DESIGNATON PER STRUCTURE COMMISSION | Si/Al2 Molar Ratio | TOTAL mmol NH$_3$/g (*160-550° C., **150-550° C., ***200-550° C.) |
|---|---|---|---|
| SAPO-11 LC | AEL | 0 | *0.341 |
| Zeolite beta | BEA | 25 | *0.481 |
| Rare earth exchange Y-54 | FAU | 5 | *1.178 |
| Rare earth exchange-LZ-210 | FAU | 6.5 | **1.033 |
| Acid wash LZY-74 | FAU | 10 | **1.057 |
| LZY-84 | FAU | 5.5 | **0.754 |
| Acid wash LZY-74 | FAU | 10 | **0.897 |
| Mordenite | MOR | 21 | **0.604 |
| UZM-8 (1$^{ST}$ Sample) | Not Determined | 20 | ***0.549 |
| UZM-8 (6$^{th}$ Sample) | Not Determined | 20 | ***0.418 |
| MCM-22 | MWW | 30 | ***0.535 |

Separate and apart from the NH$_3$-TPD acidity level, it has also been determined that the minimum acidity level can be quantified using a pyridine IR method of determining acidity including both Lewis acid and Brønsted acidity at 150° C. to be equal to or greater than 0.1 AU/mg of catalyst on an absolute basis for the powder form of the catalyst material of the outer layer. The results of the acidity measurements for various zeolites are shown in Table 3.

TABLE 3

| Brønsted Acid by Py-IR data | | |
|---|---|---|
| Zeolite Powders | structure | 150° C. |
| SAPO-11 | AEL | 0.087 |
| Beta | BEA | 0.215 |
| LZY-84 | FAU | 0.458 |
| Mordenite (Si/Al = 15) | MOR | 0.704 |
| MCM-22 | MWW | 0.496 |
| UZM-8 | N.D. | 0.26 |
| UZM-8 | N.D. | 0.213 |

Based upon these acidity levels the following catalyst will be suitable for serving as an outer layer for CHP decomposition: zeolite beta, FAU, MWW, UZM-4/BPH, UZM-5/UFI, UZM-8, ZSM-18/MEI, MOR, MTW, SPA and Cs salts of heteropoly acid. In a preferred form of the invention, the outer layer will have a volumetric ratio from about 0.17 to about 0.62 of the entire catalyst particle, more preferably from about 0.235 to about 0.503, and most preferably from about 0.289 to about 0.503.

Example 4

In Runs 19 to 30, the catalyst samples made using conventional extrusion technology in order to screen various acidic species as potential candidates for the layering process, set forth in Table 4 below, were screened for activity and selectivity. Zeolite beta was synthesized in accordance with the disclosure in U.S. Pat. No. 5,723,710. The as synthesized beta was acid washed in the presence of ammonium salt to lower sodium below 250-wppm with minimal de-alumination.

UZM-4 was synthesized using the procedure described in U.S. Pat. No. 6,419,895, and modified to UZM-4M in accordance with the procedure described in U.S. Pat. No. 6,776,975. Specifically, the UZM-4 was treated with a ammonium hexafluorosilicate (AFS) treatment, in an ammonium ion exchange reactor, to increase the silica to alumina ratio. The effluent from the ion exchange was treated by steaming and acid extraction in the presence of ammonium nitrate to further increase the silica to alumina ratio to 15.5 to greatly improve the thermal stability of the catalyst to form UZM-4M.

UZM-5 was synthesized in accordance with U.S. Pat. No. 6,613,302, and then subjected to an ammonium exchange to remove sodium and formed into an extrudate.

UZM-8 was synthesized in accordance with the disclosure of U.S. Pat. No. 6,756,030 having a silica to alumina ratio of 20. The as synthesized UZM-8 was subjected to an ammonium ion exchange to lower the sodium contents below 250-wppm on a volatile free basis, before being formed into an extrudate.

Mordenite was obtained from PQ Corporation, and was directly formulated into catalyst.

MTW was synthesized in accordance with the disclosure of U.S. Pat. No. 6,872,866 to obtain a catalyst with a silica to alumina ratios ranging from 20 to 45. The MTW was then formed into an extrudate, calcined, and subjected to an ammonium ion exchange. Then this product was calcined again to lower the sodium content to convert the catalyst from an ammonium salt form to an acid form.

MFI with a silica to alumina ratio of 38 is commercially available from UOP. MFI with a silica to alumina ratio of 23 and 80 were obtained from PQ Corporation.

Zeolite X is a commercially available from the Dow Chemical Company. The acquired material was treated to an ammonium ion exchange to lower the sodium content of the starting material.

Zeolite Y starting material having a silica to alumina ratio of 5.0 was obtained from the PQ Corporation. The starting material was treated to an ammonium ion exchange to remove approximately 75% sodium. The reduced sodium product was treated by steaming at 600° C. and then acid extracted in the presence of ammonium ion to increase the bulk silica alumina ratio to about 8.5 and the framework silica to alumina ratio to about 10 as determined by XRD.

Solid phosphoric acid ready for testing can be obtained from the Innophos Corporation located in Kentucky or Houston, Tex.

The zeolites were prepared for testing in the following typical manner. An amount of $Al_2O_3$ equivalent to 15 wt % of total powder blend on a volatile free basis was peptized using 70 wt % $HNO_3$, using a $HNO_3$ to $Al_2O_3$ ratio (w/w) of 0.17, to form a gelatin binder. The binder was added to a powder blend consisting of one of the zeolites described above, $Al_2O_3$ and Methocel, in an amount of 0.5 wt % of the total powder blend as an extrusion aid in a muller. Additional water was added to the mixture of $Al_2O_3$ binder and the powder, while mixing. Mixing was continued until a doughy consistency, suitable for extrusion, was achieved. The dough formed was extruded into 1/16" diameter pellets which were then calcined in a flowing air at approximately 550 to 600° C. over a period of 1 to 4 hours.

In the case of zeolite X and Y, Ludox silica was used as a binder to form extrudate. The formed extrudate was dried, calcined, ammonium exchanged to remove residual sodium inherent from Ludox silica. This material was calcined again to convert the zeolite from an ammonium form to an acidic form (proton).

In the case of MFI(38), the zeolite was formed into a sphere using $AlPO_4$ binder at 67/33 zeolite/binder formulation following an oil dropping technique.

Run 19 utilized a zeolite beta having a composition as specified in Table 4. Runs 20-30 utilized acidic materials other than beta zeolite as specified in Table 4. The catalysts were tested using the following experimental set up. Approximately 4 gms of a 20-40 mesh catalyst was added to 36 cc of a 1:1 molar mixture of acetone/phenol in a 50 cc stirred glass vessel operating as a continuous stirred tank reactor (CSTR) system to simulate the environment of a commercial decomposer reactor. The temperature of the mixture is then raised to about 55° C. to 70° C. and approximately 4 gms of an 85 wt % CHP concentrate solution derived from a commercial phenol unit (see reference numeral 21 of FIG. 1) was fed as a source of fresh CHP into the reaction mixture in about 30 seconds. Reaction products and temperatures were monitored during the course of the runs to determine the extent of the reaction and the product selectivity over approximately 25 minutes of total reaction time. Continuous circulation of the reaction products was maintained throughout the course of the run to control the strong exothermic heat of reaction that occurs and to simulate CSTR reactor conditions. Results obtained are described as followed with detailed catalysts and product yields and selectivities shown in the Table 4 at a reaction time of 25 minutes.

Run 19 utilizing beta zeolite showed good activity and selectivity as an unlayered material which was subjected to further enhancement using the layering process demonstrated in Example 3. Runs 20 to 24 also showed good activity and selectivity as unlayered materials and is expected to be further enhanced using the layering process demonstrated in Example 3.

Run 20 utilizing a material known as solid phosphoric acid or SPA is a non-zeolitic material that, when layered, would further enhance its performance. Runs 25-30 utilizing MFI, X and Y zeolites are alternative acidic materials such as SAPO-11 described previously in Example 3 that would not likely be enhanced sufficiently by the layering process to be acceptable candidates for the CHP decomposition process due to low activity and selectivity demonstrated in the screening process of Example 4.

TABLE 4

| Run # | CATALYST BINDER Material | Mesh Size | ACIDIC MATERIAL Material | Weight Fraction | Temperature Deg. C. | Residual CHP (%) t = 25 min | AMS Yield (%) | AMS Selectivity (%) |
|---|---|---|---|---|---|---|---|---|
| 19 | gamma-$Al_2O_3$ | 20-40 | Beta | 0.70 | 63.6 | 0.0 | 83.3 | 91.2 |
| 20 | silica phosphate | 20-40 | H3PO4 | | 55.1 | 0.0 | 66.0 | 76.1 |
| 21 | gamma-$Al_2O_3$ | 20-40 | Mordenite | 0.75 | 60.8 | 1.5 | 82.9 | 91.4 |
| 22 | gamma-$Al_2O_3$ | 20-40 | UZM-4M | 0.70 | 55.1 | 0.0 | 83.6 | 85.9 |
| 23 | gamma-$Al_2O_3$ | 20-40 | UZM-8/Beta (70/30) | 1.00 | 55.1 | 0.0 | 72.3 | 73.8 |
| 25 | AlPO4 | 20-40 | MFI (SiAl2 = 38) | 0.67 | 80.3 | 68.9 | 3.4 | 10.2 |

TABLE 4-continued

| Run # | CATALYST BINDER | | ACIDIC MATERIAL | | Temperature Deg. C. | Residual CHP (%) t = 25 min | AMS Yield (%) | AMS Selectivity (%) |
|---|---|---|---|---|---|---|---|---|
| | Material | Mesh Size | Material | Weight Fraction | | | | |
| 26 | gamma-Al$_2$O$_3$ | 20-40 | MFI (SiAl2 = 23) | 0.75 | 80.3 | 71.5 | 16.3 | 64.0 |
| 27 | gamma-Al$_2$O$_3$ | 20-40 | MFI (SiAl2 = 80) | 0.75 | 80.3 | 73.5 | 6.1 | 11.9 |
| 28 | gamma-Al$_2$O$_3$ | 20-40 | MTW | 0.50 | 80.3 | 90.7 | 34.4 | 90.6 |
| 29 | SiO2 | 20-40 | X | 0.80 | 55.1 | 72.1 | 24.1 | 71.9 |
| 30 | SiO2 | 20-40 | Y | 0.80 | 55.1 | 0.0 | 55.6 | 55.7 |

Best results observed in this testing are better than any known commercial decomposer operation using trace sulfuric acid with AMS yields ranging from 78 to about 81% and an overall cumene/phenol consumption ratio of about 1.31. Note that Run 5 showed an AMS yield in excess of 86% which is equivalent to an overall cumene/phenol consumption ratio of about 1.29 if the resultant AMS is hydrogenated and recycled as cumene back to the oxidation section of the process which is typically what is practiced in commercial operation. The only way, known to the inventors hereof, to achieve such a yield with the conventional sulfuric acid technology is to use acetone recycled as a diluent in the decomposer section (at molar ratio significantly greater than 1) which would be at an added cost and is typically difficult to justify.

The foregoing description, drawings and illustrative embodiment clearly illustrate the advantages encompassed by the process of the present invention and the benefits to be afforded with the use thereof.

The invention claimed is:

1. A process for decomposing a cumene hydroperoxide to produce phenol and acetone comprising:
    introducing a process stream containing cumene hydroperoxide into a reaction vessel;
    contacting the process stream with catalyst particles to form a product stream, the catalyst particles having an inner core selected from one or more of refractory inorganic oxides, silicon carbide, and metals; and an outer layer of an acidic material bonded to the inner core;
    introducing into the reaction vessel a cooled stream comprising unreacted cumene hydroperoxide, phenol, and acetone and contacting the cooled stream with the process stream; and
    withdrawing a portion of the product stream from the reactor and recovering phenol and acetone products.

2. The process of claim 1 wherein the outer layer has a volumetric fraction of the entire catalyst particle from about 0.17 to about 0.62.

3. The process of claim 1 wherein the outer layer has a volumetric fraction of about 0.235 to about 0.503 of the entire catalyst particle.

4. The process of claim 1 wherein the outer layer is selected from the group consisting of zeolite beta, FAU, MWW, UZM-4, UZM-5, UZM-8, ZSM-18, MOR, MTW, SPA and Cs salts of heteropoly acid.

5. The process of claim 1 wherein the outer layer is a zeolite beta.

6. The process of claim 1 wherein the inner core and the outer layer of the catalyst particles form a particle having an average particle diameter of from about 0.1 mm to about 5.5 mm.

7. The process of claim 1 wherein the outer layer has an acidity level when measured by NH$_3$-TPD of equal to or greater than 0.36 mmoles NH$_3$ per gram catalyst at 150 to 550° C. based on using a powder form of the acidic material.

8. The process of claim 1 is conducted without the use of a liquid mineral acid.

9. The process of claim 1 wherein the ratio of the flow rate of the cooled stream to the process stream is from about 5:1 to 100:1.

10. The process of claim 1 wherein the product stream contains dicumylperoxide and wherein the process includes converting the dicumylperoxide to cumene hydroperoxide and dimethylphenylcarbinol.

11. The process of claim 10 further comprising converting the dimethylphenylcarbinol to alpha-methylstyrene.

12. A process for decomposing a cumene hydroperoxide to produce phenol and acetone comprising:
    introducing a process stream containing cumene hydroperoxide into a reaction vessel;
    contacting the process stream with catalyst particles to form a product stream, the catalyst particles having an inner core selected froth one or more of refractory inorganic oxides, silicon carbide, and metals; and an outer layer bonded to the inner core, the outer layer comprising a material selected from the group consisting of zeolite beta, FAU, MWW, UZM-4, UZM-5, UZM-8, ZSM-18, MOR, MTW, SPA and Cs salts of heteropoly acid; and
    withdrawing a portion of the product stream from the reactor and recovering phenol and acetone products.

13. The process of claim 12 is conducted without the use of a liquid mineral acid.

14. The process of claim 12 further comprising introducing into the reaction vessel a cooled stream comprising unreacted cumene hydroperoxide, phenol and acetone and contacting the cooled stream with the process stream.

15. The process of claim 12 wherein the product stream contains dicumylperoxide and wherein the process includes converting the dicumylperoxide to cumene hydroperoxide and dimethylphenylcarbinol.

16. The process of claim 15 further comprising converting the dimethylphenylcarbinol to alpha-methylstyrene.

17. The process of claim 12 wherein the outer layer is a zeolite beta.

18. A process for decomposing a cumene hydroperoxide to produce phenol and acetone comprising:
    introducing a process stream containing cumene hydroperoxide into a reaction vessel;
    contacting the process stream with catalyst particles to form a product stream, the catalyst particles having an inner core selected from one or more of refractory inorganic oxides, silicon carbide, and metals; and an outer layer of an acidic material bonded to the inner core; and
withdrawing a portion of the product stream from the reactor and recovering phenol and acetone products;
wherein the product stream contains dicumylperoxide and the process further comprises converting the dicumylperoxide to cumene hydroperoxide and dimethylphenylcarbinol.

19. The process of claim 18 further comprising converting the dimethylphenylcarbinol to alpha-methylstyrene.

20. The process of claim 18 wherein the outer layer is selected from the group consisting of zeolite beta, FAU, MWW, UZM-4, UZM-5, UZM-8, ZSM-18, MOR, MTW, SPA and Cs salts of heteropoly acid.

* * * * *